United States Patent [19]

Aketa et al.

[11] 4,312,816

[45] Jan. 26, 1982

[54] PROCESS FOR PREPARING OPTICALLY ACTIVE α-CYANO-3-PHENOXYBENZYL 2-(4-CHLOROPHENYL)ISOVALERATE

[75] Inventors: Kohichi Aketa; Yukio Suzuki, both of Toyonaka, Japan; Nobuo Ohno, Austin, Tex.; Isamu Nakayama; Takashi Kato, both of Toyonaka, Japan

[73] Assignee: Sumitomo Chemical Company, Limited, Osaka, Japan

[21] Appl. No.: 922,476

[22] Filed: Jul. 7, 1978

[30] Foreign Application Priority Data

| Jul. 7, 1977 | [JP] | Japan | 52-81833 |
| Oct. 7, 1977 | [JP] | Japan | 52-121242 |
| Oct. 11, 1977 | [JP] | Japan | 52-122078 |

[51] Int. Cl.$^3$ ............................................. C07C 121/75
[52] U.S. Cl. ................................. 260/465 D; 424/304
[58] Field of Search ................................. 260/465 D

[56] References Cited

U.S. PATENT DOCUMENTS

| 2,388,688 | 11/1945 | Hass | 562/401 |
| 3,405,159 | 10/1968 | Krieger et al. | 260/465 |
| 3,857,889 | 12/1974 | Leigh | 562/401 |
| 3,996,244 | 12/1976 | Fujimoto et al. | 260/332.2 |
| 4,133,826 | 1/1979 | Warnant et al. | 260/465 D |
| 4,213,916 | 7/1980 | Davies et al. | 260/465 D |

FOREIGN PATENT DOCUMENTS

| 853866 | 10/1977 | Belgium . |
| 853867 | 10/1977 | Belgium . |
| 50-25544 | 3/1975 | Japan . |
| 54-109945 | 8/1979 | Japan . |
| 1448228 | 9/1976 | United Kingdom . |

OTHER PUBLICATIONS

Elliott et al., *Pesticidal Science,* vol. 9, pp. 105–111, (1978).
Itaya et al., *ACS Symposium Series,* No. 42, "Synthetic Pyrethroids", p. 45, (1977).
Yoshioka, *Rev. Plant Protect. Res.,* 11, p. 39, (1978).
Eliel, *Stereochemistry of Carbon Compounds,* pp. 47–83, (1962), published by McGraw-Hill Book Co., (N.Y.).
Hauser et al., *J.A.C.S.,* vol. 80, pp. 4345–4348, (1958).
Cram et al., *J.A.C.S.,* vol. 86, pp. 5457–5465, (1964).
Aaron et al., *J. Org. Chem.,* vol. 32, pp. 2797–2803, (1967).
Dale et al., *J.A.C.S.,* vol 90 (14), pp. 3732–3738, (1968).
Halpern et al., *Tetrahedron,* vol. 27, pp. 1173–1184, (1971).

*Primary Examiner*—Dolph H. Torrence
*Attorney, Agent, or Firm*—Sughrue, Mion, Zinn, Macpeak and Seas

[57] ABSTRACT

A process for isomerizing optically active α-cyano-3-phenoxybenzyl 2-(4-chlorophenyl)isovalerate at the asymmetric carbon atom of the 3-phenoxybenzyl moiety, and a process for obtaining (S)-α-cyano-3-phenoxybenzyl (S)-2-(4-chlorophenyl)isovalerate from (R, S)-α-cyano-3-phenoxybenzyl (S)-2-(4-chlorophenyl)isovalerate.

60 Claims, No Drawings

PROCESS FOR PREPARING OPTICALLY ACTIVE α-CYANO-3-PHENOXYBENZYL 2-(4-CHLOROPHENYL)ISOVALERATE

BACKGROUND OF THE INVENTION

1. Field of the Invention

This invention relates to a process for isomerizing optically active α-cyano-3-phenoxybenzyl 2-(4-chlorophenyl)-isovalerate at the asymmetric carbon atom of the 3-phenoxy-benzyl moiety, and to a process for obtaining (S)-α-cyano-3-phenoxybenzyl (S)-2-(4-chlorophenyl)isovalerate from (R, S)-α-cyano-3-phenoxybenzyl (S)-2-(4-chlorophenyl)isovalerate.

2. Description of the Prior Art

α-Cyano-3-phenoxybenzyl 2-(4-chlorophenyl)isovalerate of the formula (I):

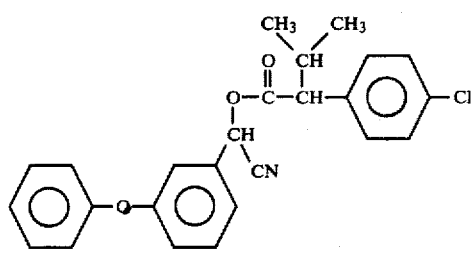

which has a low toxicity to mammals and a broad spectrum of insecticidal activity (e.g., as disclosed in Japanese patent application (OPI) No. 26425/74, U.S. Pat. No. 3,996,244) contains two asymmetric carbon atoms in the molecule thereof, and, therefore, includes four optical isomers.

α-Cyano-3-phenoxybenzyl 2-(4-chlorophenyl)isovalerate of the formula (I) above will be referred to hereinafter as "fenvalerate"; (R, S)-α-cyano-3-phenoxybenzyl (S)-2-(4-chlorophenyl)isovalerate, as "fenvalerate A"; (S)-α-cyano-3-phenoxybenzyl (S)-2-(4-chlorophenyl-)isovalerate, as "fenvalerate Aα"; (R)-α-cyano-3-phenoxybenzyl (S)-2-(4-chlorophenyl)-isovalerate, as "fenvalerate Aβ"; (S)-α-cyano-3-phenoxybenzyl (R)-2-(4-chlorophenyl)isovalerate, as "fenvalerate Bα"; and (R)-α-cyano-3-phenoxybenzyl (R)-2-(4-chlorophenyl-)isovalerate, as "fenvalerate Bβ".

The relationship of the absolute configuration of the asymmetric carbon atom on the acid moiety to the insecticidal activity of the ester has already been elucidated, and a process for preparing (S)-2-(4-chlorophenyl)isovaleric acid which provides an ester having a greater insecticidal effect is known (Miyakado et al., Agr. Bio. Chem., 39, 267 (1975)). Miyakado et al., supra, describes a method of optical resolution of α-isopropylphenylacetic acids, and the insecticidal activity of phenylacetic acid esters having an optically active acid moiety.

The relationship of the absolute configuration of the asymmetric carbon atom on the alcohol moiety to the insecticidal activity of the ester is disclosed in Japanese patent application No. 135013/76 which also describes a method for preparing ester having an optically active alcohol moiety. Japanese patent application No. 99071/76 (corresponding to U.S. Ser. No. 825,507, filed Aug. 17, 1977) discloses a process for producing a fenvalerate isomer having an optically active alcohol moiety by chromatographing fenvalerate A on a silica gel column to separate fenvalerate A into fenvalerate Aα and fenvalerate Aβ. The method disclosed in Japanese patent application No. 135013/76 proceeds through optically active 3-phenoxymandelic acid obtained by optical resolution of 3-phenoxymandelic acid. Although these methods are suitable on a laboratory scale, they are far from being industrially feasible.

Fenvalerate Aα is an excellent compound having an insecticidal activity of about 4 times greater than the racemic fenvalerate (e.g., as disclosed in Japanese patent application No. 99071/76 (corresponding to U.S. Ser. No. 825,507, filed Aug. 17, 1977)).

SUMMARY OF THE INVENTION

This invention in one embodiment provides a process for separating fenvalerate Aα as crystals from fenvalerate A without the necessity for the use of an isomerization catalyst (hereinafter "Process A").

The invention in another embodiment provides a process for isomerizing optically active fenvalerate at the asymmetric carbon atom on the alcohol moiety thereof by dissolving optically active fenvalerate in a protonic solvent, or dissolving optically active fenvalerate in a solvent in the presence of a basic catalyst (hereinafter "Process B").

According to the invention, fenvalerate A can be converted to fenvalerate Aα almost quantitatively by dissolving the fenvalerate Aβ-rich mother liquor remaining after separation of the fenvalerate Aα crystals in a solvent, isomerizing the fenvelerate A at the asymmetric carbon atom on the alcohol moiety in the presence or absence of a basic catalyst to return the ratio between fenvalerate Aα and fenvalerate Aβ to an equilibrium ratio, and again subjecting the mixture to a crystallization treatment. Process A or a combination of Processes A and B can be used to produce fenvalerate Aα substantially free from fenvalerate Aβ.

The present invention also provides in a further embodiment a process comprising Process A described above in which the crystallization of fenvalerate Aα is performed in the presence of a basic catalyst (hereinafter "Process C"). The basic catalyst causes the isomerization at the asymmetric carbon atom on the alcohol moiety. By adding this catalyst to the crystallization system of fenvalerate Aα, the fenvalerate Aβ present in the mother liquor in a larger proportion than the equilibrium ratio is converted to fenvalerate Aα as a result of the isomerization at the asymmetric carbon atom on the alcohol moiety. It is, thus, possible to obtain fenvalerate Aα crystals in a larger amount than that originally present. According to Process C, 70 to 90 parts of fenvalerate Aα crystals can be obtained per 100 parts of the starting fenvalerate A.

The present invention provides in an even further embodiment a process for obtaining fenvalerate A containing a major proportion of fenvalerate Aα by recovering the fenvalerate Aα obtained by Process C together with fenvalerate A present in the mother liquor (hereinafter "Process D"). The fenvalerate A contained in the mother liquor from which fenvalerate Aα crystals have been separated by filtration or other means in Process C naturally contains fenvalerate Aα in an amount corresponding to about half of that of fenvalerate A. If the fenvalerate A In the mother liquor recovered in Process C is re-utilized in Process C, the losses are decreased. However, this is not practical in view of the fact that the impurities are more concentrated. In Process D, both the fenvalerate Aα crystals and the mother liquor are recovered, and fenvalerate Aα present in the mother liquor is also utilized effectively. Concentration of the mixture directly after crystallization is a simple procedure. However, since the catalyst still remains in the system, care must be taken as to the possibility of isomerization of fenvalerate Aα to fenvalerate A.

This possibility can be eliminated by first deactivating the catalyst with an acidic substance, for example, and then concentrating the mixture. However, the deactivated catalyst remains in the final product. If the catalyst, either as such or deactivated, is insoluble, the catalyst can be removed by means such as filtration. When the catalyst, either as such or deactivated, is water-soluble, the catalyst can be removed conveniently by adding a water-insoluble solvent, or a mixture of a water-soluble solvent and a water-insoluble solvent, and then washing the solution. Alternatively, after crystallization of the fenvalerate Aα, the product can be applied for formulation either as such or after only deactivating the catalyst.

Thus, according to Process D, fenvalerate A composed of 45 to 50 parts of fenvalerate Aα and 55 to 50 parts of fenvalerate Aβ can be converted to fenvalerate Aα-rich fenvalerate A almost quantitatively.

In Processes A, C and D, the addition of a seed crystal is not essential, but in commercial operation, seeding is desirable in order to perform the crystallization smoothly. Seeding is not always necessary in a continuous commercial operation because crystals remain in the reactor.

DETAILED DESCRIPTION OF THE INVENTION

In investigations on a process for producing a fenvalerate isomer having an optically active alcohol moiety, it was found that by adding a seed crystal of fenvalerate Aα, fenvalerate Bβ or a mixture of both to a solution of fenvalerate A, only the fenvalerate Aα is selectively crystallized out.

As is the case with pyrethroid-type esters, the crystallization of the above compound cannot be inferred at all from the properties of the racemic fenvalerate which is a viscous oily substance.

Fenvalerate Aα: m.p. 57.9° C., $[\alpha]_D^{21} -11.2°$ (in CHCl$_3$, c=6.5)

Fenvalerate Bβ: m.p. 59.6° C., $[\alpha]_D^{24} +12.5°$ (in CHCl$_3$, c=3.8)

For example, in α-cyano-3-phenoxybenzyl 2,2-dimethyl-3-(2,2-dichlorovinyl)cyclopropane carboxylate, which is a pyrethroid-type ester having the same alcohol moiety as the above compound, no ester thereof having a d-trans (1R, 3S) acid moiety and an (S), (R) or racemic alcohol moiety has been known to crystallize. However, both a 1:1 (by weight) mixture (m.p. 75.0°-76.8° C.) of an ester having a d-trans acid moiety and an (R) alcohol moiety and an ester having an l-trans (1S, 3R) acid moiety and an (S) alcohol moiety and a 1:1 (by weight) mixture (m.p. 78.5°-80° C.) of an ester having a d-trans acid moiety and an (S) alcohol moiety and an ester having an l-trans acid moiety and an (R) alcohol moiety have been obtained as crystals.

It was also found that in α-ethynyl-3-phenoxybenzyl 2-(4-chlorophenyl)isovalerate, which is a pyrethroid-type ester having a very similar chemical structure to the above compound, a mixture (m.p. 46°-47° C.) of esters having a racemic acid moiety and a racemic alcohol moiety, a mixture of two diastereomers thereof (each being racemic), and an ester thereof having an optically active acid moiety are crystalline at room temperature. When the ester mixture having a racemic acid moiety and a racemic alcohol moiety is recrystallized from hexane, a diastereomer having a melting point of 87 to 88° C. and a very weak insecticidal activity crystallize predominately. The ester recovered from the mother liquor is a diastereomer (m.p. 51°-52° C.) having a higher insecticidal activity. On the other hand, when the ester having an optically active acid moiety (m.p. 61°-62° C.) is subjected to this procedure, selective crystallization of a diastereomer is not observed.

In allethrin (i.e., allethronyl chrysanthemate) long well known as a synthetic pyrethroid-type ester which includes four diastereomers, only a diastereomer ("crystalline allethrin") consisting of an ester having a d-trans acid moiety and an l-alcohol moiety and an ester having an l-trans acid moiety and a d-alcohol moiety is known to crystallize (e.g., as disclosed in M. Matsui & I. Yamamoto, *Natural Occurring Insecticides*, M. Jacobson & D. G. Grosby Eds., pp. 38–42, Marcel Dekker, Inc., New York (1971)). No enantiomorph of "crystalline allethrin" is known to crystallize by itself.

These facts show that it is quite impossible to predict which optical isomers or a mixture thereof obtained as crystals, and that even when a certain optical isomer is obtained as crystals, it is quite impossible to predict whether that optical isomer can be selectively crystallized from a mixture of that optical isomer with other optical isomers.

Effective utilization of the mother liquor which is obtained as a by-product during the preparation of fenvalerate having an optically active alcohol moiety has now been studied, and it has now been found that by dissolving optically active fenvalerate having an alcohol moiety in a non-equilibrium ratio of (R)/(S) in a protonic solvent or a mixed solvent containing a protonic solvent and preferably adding a basic catalyst, or dissolving it in an aprotic solvent and then adding a basic catalyst, the asymmetric carbon atom on the alcohol moiety is rapidly isomerized. It has been generally thought that a mandelonitrile ester such as the ester described above is unstable in a protonic solvent or in the presence of a basic catalyst, and a cleavage of the ester linkage, or the decomposition of the nitrile group tends to occur. It has now been found, however, that the intended isomerization takes place predominantly in the ester described above.

Isomerization of an optically active aliphatic nitrile in the presence of a basic catalyst has already been reported (e.g., as described in J. Am. Chem. Soc., 86, p. 5457 (1964)). To the best of the inventors' knowledge, however, isomerization of an ester such as the ester described above in solution has not been reported so far.

It has also been found in this invention that by adding a basic catalyst to a solution of fenvalerate A, the crystallization of fenvalerate Aα and the isomerization of fenvalerate Aβ in the mother liquor can be performed simultaneously, and fenvalerate Aα can be obtained in a high yield.

Turning now to this invention in detail, in Process A, any solvent in which fenvalerate A is readily soluble and which is capable of dissolving fenvalerate Aα only to a moderately small extent can be used. Examples of solvents which can be used are lower alcohols having 1 to 6 carbon atoms such as methanol or ethanol, and aliphatic or alicyclic hydrocarbons such as pentane, hexane, heptane, cyclohexane and methylcyclohexane, either alone or as mixtures thereof; and mixtures of these solvents with aromatic hydrocarbons such as benzene, toluene and xylene, with lower alcohols such as methanol or ethanol, with mixed solvents containing lower alcohols being preferred. Methanol is the most preferred solvent.

Suitable aprotic solvents which can be used in Process B include, for example, aliphatic hydrocarbons such as pentane, hexane or heptane, alicyclic hydrocarbons such as cyclohexane or methylcyclohexane, aromatic hydrocarbons such as benzene, toluene or xylene, halogenated hydrocarbons such as chlororform, dichloromethane or carbon tetrachloride, and aprotic polar solvents such as ethyl acetate or acetone. Examples of suitable protonic solvents which can be used are alcohols such as methanol, ethanol or octanol, and mixtures of these with each other. Mixtures of these protonic solvents with aprotic solvents can also be used. Preferred solvents are lower alcohols such as methanol or ethanol, mixed solvents containing lower alcohols, aliphatic hydrocarbons such as pentane, hexane or heptane, alicyclic hydrocarbons such as cyclohexane or methylcyclohexane, and mixtures of aliphatic or alicyclic hydrocarbons with aromatic hydrocarbons such as benzene, toluene or xylene or with other solvents. Advantageously, these solvents can be used as common solvents in the combination of Processes A and B to be described hereinbelow. Among these solvents, methanol is an especially preferred solvent. A catalyst is not particularly required when a protonic solvent such as an alcohol is used, but the isomerization is preferably performed in the presence of a basic catalyst.

When the base used as a catalyst can dissolve optically active fenvalerate, a solvent is not always necessary.

The catalyst may be optionally selected from basic substances such as nitrogen-containing bases, phosphorus-containing bases, metal oxides, metal hydroxides, salts of metals with weak acids such as carbonic acid, silicic acid or hydrocyanic acid, and base-type ion exchange resins. Specific examples of catalysts which can be used include ammonia; aliphatic amines such as methylamine, ethylamine, n-propylamine, isopropylamine, n-butylamine, n-pentylamine, diethylamine, di-n-propylamine, di-n-butylamine, triethylamine, tri-n-propylamine, tri-n-butylamine, cyclohexylamine, and ethanol-amine; aromatic amines such as aniline, 1-naphthylamine and 2-naphthylamine; quaternary ammonium salts such as tetramethyl ammonium hydroxide, tetraethyl ammonium hydroxide and tetra-n-propyl ammonium hydroxide; nitrogen-containing heterocyclic compounds such as pyridine, quinoline, pyrrolidine and piperidine; phosphorus-containing bases such as triphenyl phosphine and tri-n-butyl phosphine; metal oxides such as calcium oxide, magnesium oxide, beryllium oxide, zinc oxide, silicon dioxide and alumina; metal hydroxides such as sodium hydroxide, potassium hydroxide, magnesium hydroxide and calcium hydroxide; weak acid metal salts such as sodium carbonate, potassium carbonate, barium carbonate and potassium cyanide; talc; bentonite; the bases described above adsorbed on silica gel, alumina or activated carbon; and base-type ion exchange resins which have a basic group such as an amino group or a quaternary ammonium group. Suitable commercially available base-type ion exchange resins which can be used include "DOWEX 2×8" (a trademark for a product of the Dow Chemical Company, which is a strong base-type ion exchange resin made from a styrene-divinylbenzene copolymer having a quaternary ammonium group (—NR₃⁻⁺+OH⁻) incorporated therein), "AMBERLITE IR-45" (a trademark for a product of the Rohm & Haas Company, which is a weak base-type anion exchange resin having—N(R)₂, —NH(R) and —NH₂ moieties as exchanging moieties), "AMBERLITE IRA-93" (a trademark for a product of the Rohm & Haas Company, which is a weak base-type anion exchange resin (MR-type) having an —N(CH₃)₂ moiety as an exchanging moiety), "AMBERLIST A-21" (a trademark for a product of the Rohm & Haas Company, which is a weak base-type anion exchange resin (MR-type) having an —N(CH₃)₂ moiety as an exchanging moiety and which is usefull for non-aqueous solutions), and "AMBERLIST A-27" (a trademark for a product of the Rohm & Haas Company, which a strong base-type anion exchange resin (OH-type) having an

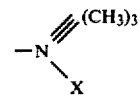

moiety as an exchanging moiety and which is useful for non-aqueous solutions).

From the standpoint of ease of removal of the catalyst after the isomerization reaction, those basic substances which are substantially insoluble in the solvents described above, especially base-type ion exchange resins, are preferred. It is to be understood that the basic catalyst is not limited to the materials exemplified hereinabove, and other substances can also be selected without departing from the spirit and scope of the invention.

In this invention, the catalyst may be added to the solution containing the fenvalerate A to be isomerized, or the solution containing the fenvalerate A may be passed through a column packed with the catalyst.

Suitable temperatures at which the isomerization can be accomplished are those at which the ester does not undergo any significant decomposition. The rate of isomerization is higher at higher temperatures. Preferably, the isomerization temperature ranges from about −50° C. to the boiling point of the solvent, more preferably from −20° C. to 150° C.

The optically active fenvalerate in Process B can have any ratio of (S)/(R) as to the alcohol moiety of the fenvalerate.

Fenvalerate Aα can be prepared using a combination of Processes A and B by a combination of the following steps, but the preparation of fenvalerate Aα is not limited thereto:

(1) adding a seed crystal of fenvalerate Aα or fenvalerate Bβ to a fenvalerate A solution supersaturated with regard to fenvalerate Aα thereby to crystallize fenvalerate Aα;

(2) separating the fenvalerate Aα crystals obtained in step (1) from the mother liquor using an operation such as filtration;

(3) subjecting the mother liquor obtained in step (2) or fenvalerate Aβ-rich fenvalerate A obtained by concentrating the motor liquor described above to an isomerization by dissolving the mother liquor in a protonic solvent such as a lower alcohol or a mixed solvent containing a protonic solvent, preferably in the presence of a basic substance, or by dissolving the mother liquor in a solvent in the presence of a basic substance as a catalyst;

(4) preparing a solution supersaturated with respect to fenvalerate A isomerized in step (3) so as to subject the fenvalerate A again to step (1), where the supersaturated solution can be prepared, for example, by concentrating the solution (e.g., by distilling off the solvent), or by adding additional fenvalerate A to the solution, or by cooling the solution.

In Processes C and D, any solvents in which fenvalerate A is readily soluble and in which fenvalerate Aα is dissolved only to a moderately small extent can be used. Preferred solvents are lower alcohols such as methanol or ethanol and mixed solvents containing lower alcohols. Other examples of solvents which can be used include aliphatic hydrocarbons such as pentane, hexane or heptane, alicyclic hydrocarbons such as cyclohexane or methylcyclohexane, mixtures of these solvents, mixtures of at least one of these solvents with an aromatic hydrocarbon such as benzene, toluene or xylene, and mixtures of these hydrocarbons (or mixtures thereof) with lower alcohols. The use of aromatic hydrocarbons alone and the use of acetonitrile alone are not suitable in this invention since they dissolve fenvalerate Aα to a very large extent. Methanol and ethanol are preferred of the lower alcohols, and methanol is most preferred. When methanol is used, the water content in the methanol should preferably be limited to below 5%. Advantageous results are not obtained when isopropanol or hydrous isopropanol is used.

A suitable concentration of fenvalerate A in the solution is between about 1 and about 90% by weight in view of the yield of the crystals obtained and the rate of crystallization, and preferably the concentration is 20 to 70% by weight.

The basic substance as a catalyst can be selected from a wide range of basic substances such as nitrogen-containing bases, phosphorus-containing bases, strong bases, and base-type ion exchange resins. Specific examples of suitable basic substances which can be used include ammonia; aliphatic amines such as methylamine, ethylamine, n-propylamine, n-butylamine, n-pentylamine, diethylamine, di-n-propylamine, di-n-butylamine, triethylamine, tri-n-propylamine, tri-n-butylamine, cyclohexylamine, and ethanolamine; aromatic amines such as aniline, 1-naphthylamine and 2-naphthylamine; quaternary ammonium salts such as tetramethyl ammonium hydroxide, tetraethyl ammonium hydroxide and tetra-n-propyl ammonium hydroxide; nitrogen-containing heterocyclic compounds such as pyridine, quinoline, pyrrolidine and piperidine; phosphorus-containing bases such as triphenyl phosphine and tri-n-butyl phosphine; strong bases such as alkali metal or alkaline earth metal hydroxides (e.g., sodium hydroxide or potassium hydroxide), alkali metal or alkaline earth metal alcoholates (e.g., sodium methylate or sodium ethylate), alkali metal or alkaline earth metal amides (e.g., sodium amide or magnesium amide), and alkali metal or alkaline earth metal hydrides (e.g., sodium hydride, potassium hydride or lithium aluminum hydride); and base-type ion exchange resins (e.g., DOWEX 2×8 or AMBERLITE IR-45).

Of these bases, ammonia and amines are preferred from the standpoint of yield of the crystals, etc. Ammonia and triethylamine are most preferred.

A suitable amount of the catalyst is about 0.01 to about 100 mol%, preferably 0.1 to 50 mol%, based on fenvalerate A. A suitable isomerization temperature is about −50° to about 50° C. from the standpoint of the yield of the crystals and the rate of crystallization. Preferably, the isomerization temperature is −30° to 15° C. Desirably, the solution is stirred while isomerization is carried out, but stirring is not essential. The fenvalerate A used in Process C or D can contain any ratio of fenvalerate Aα and fenvalerate Aβ.

The following Examples are given to illustrate the present invention in more detail. However, the present invention should not be construed as being limited to these examples. Unless otherwise indicated, all parts, percents, ratios and the like are by weight.

In these Examples, the (R) isomer (fenvalerate Aβ) and the (S) isomer (fenvalerate Aα) of the alcohol moiety were analyzed by gas chromatography under the following analysis conditions.

Column: 10% silicone DC-QF-1 3 mm$\phi$×3.0 m (coated on Chromosorb AW-DMCS)
Column Temperature: 245° C.
Temperature of the Vaporizing Chamber: 250° C.
Nitrogen Pressure: 2.0 kg/cm$^2$ Under the above conditions, the retention time of the (S) isomer (fenvalerate Aα) was about 43 minutes, and the retention time of the (R) isomer (fenvalerate Aβ) was about 38 minutes.

According to this method, esters having the (R) acid moiety naturally have reverse retention time, i.e., the retention time of the ester having the (S) alcohol moiety (fenvalerate Bα) is the same as fenvalerate Aβ, and that of the ester having the (R) alcohol moiety (fenvalerate Bβ) is the same as fenvalerate Aα. Thus, when a certain proportion of the ester having the (R) acid moiety is present in the fenvalerate A used, the peak of each of the above isomers overlaps the peak of the enantiomer thereof in approximately that proportion.

The optical purity of the acid moiety of fenvalerate A was determined as follows: Fenvalerate A was hydrogenated in ethanol using platinum oxide as a catalyst to obtain (S)-2-(4-chlorophenyl)isovaleric acid which was then converted to an acid chloride using thionyl chloride. The acid chloride was converted to the l-menthol ester with l-menthol. The ratio between the two resulting diastereomers was determined by gas chromatography, and the optical purity of the acid moiety was calculated.

EXAMPLE 1

Fenvalerate A in which the alcohol moiety had a composition of 50.5% of a peak ascribable to the (R) isomer and 49.5% of a peak ascribable to the (S) isomer and the acid moiety had an optical purity of 92.8% was used as a starting material. (Unless otherwise indicated, fenvalerate A used in the other Examples had the same composition and optical purity as that used in Example 1.)

5.0 g of this starting material was dissolved in 5.0 g of ethyl alcohol, and 1 mg of a crystal of (S)-α-cyano-3-phenoxybenzyl (S)-2-(4-chlorophenyl)isovalerate was added as a seed. The mixture was allowed to stand for 4 days at −6° C. Then, the precipitated crystals were collected by filtration. The solid deposited on the filter was washed three times with 2 ml of cold ethanol (0°-5° C.). The yield of the crystals (m.p. 57.9° C.) was 1.27 g. A gas chromatographic analysis of the crystals showed that, as to the alcohol moiety of the ester, 4% of the (R) isomer and 96% of the (S) isomer were present. As to the alcohol moiety of the ester in the filtrate 65.5% of the (R) isomer and 34.5% of the (S) isomer were present.

EXAMPLE 2

The procedures of Example 1 were repeated except using a crystal of fenvalerate Bβ as a seed. The yield of the crystals was 1.32 g. Analysis of the crystals showed, as to the alcohol moiety of the ester, 3% of the (R) isomer and 97% of the (S) isomer were present.

EXAMPLE 3

The procedures of Example 1 were repeated except that 5.5 g of a mixture of benzene and n-hexane (1:5 by weight) was used instead of the ethyl alcohol. The yield of the crystals was 0.62 g. Analysis of the crystals showed, as to the alcohol moiety of the ester, 2.7% of the (R) isomer and 97.3% of the (S) isomer were present.

EXAMPLE 4

The procedures of Example 1 were repeated except that 6 g of methyl alcohol was used instead of the ethyl alcohol. The yield of the crystals was 1.78 g, and analysis of the crystals showed, as to the alcohol moiety of the ester, 4.5% of the (R) isomer and 95.5% of the (S) isomer were present.

EXAMPLE 5

5.18 g of fenvalerate A was dissolved in 5.2 g of methanol, and 1 mg of a crystal of fenvalerate Aα was added as a seed. The mixture was stirred for 1 day at 2° to 4° C. Thereafter, the precipitated crystals were collected by filtration. The solid deposited on the filter was washed twice with 3 ml of cold hexane (0°–5° C.). The yield of the crystals was 1.48 g (28.6% by weight based on the fenvalerate A used). Analysis of the crystals showed, as to the alcohol moiety of the ester, 3.4% of the (R) isomer and 96.6% of the (S) isomer were present. As to the alcohol moiety of the fenvalerate A recovered from the filtrate, 68.5% of the (R) isomer and 31.5% of the (S) isomer were present.

EXAMPLE 6

Fenvalerate Aβ in which the alcohol moiety thereof had a composition comprising 96.0% of a peak ascribable to the (R) isomer and 4.0% of a peak ascribable to the (S) isomer using the gas chromatographic analysis described above was used as a starting material.

50 mg of the fenvalerate Aβ was dissolved in 50 ml of ethyl alcohol, and the solution was stored in a glass vessel. Seven days later, a sample of the solution was analyzed by gas chromatography and the solution was found to contain, as to the alcohol moiety of the ester, 53.1% of the (R) isomer and 46.9% of the (S) isomer. The ethyl alcohol was distilled off under reduced pressure, and 48 mg of the isomerized ester was recovered.

EXAMPLE 7

500 mg of fenvalerate Aβ having the same composition as that of the fenvalerate Aβ used in Example 6 was dissolved in 50 ml of ethyl alcohol, and the solution was maintained at 40° C. for 2 days in a glass vessel. Then, the solution was cooled to room temperature (i.e., 20°–30° C., hereinafter the same), and a sample of the solution was analyzed by gas chromatography and, as to the alcohol moiety of the ester in the solution, 72.1% of the (R) isomer and 27.9% of the (S) isomer were found. The solution was concentrated under reduced pressure and 468 mg of the isomerized ester was recovered.

EXAMPLE 8

30 mg of fenvalerate Aβ having the same composition as that of the fenvalerate Aβ used in Example 6 was dissolved in 300 ml of ethyl alcohol, and the solution was stored for 30 days at −6° C. Thereafter, a sample of the solution was analyzed by gas chromatography and, as to the alcohol moiety of the ester in the solution, 64% of the (R) isomer and 36% of the (S) isomer were found. The ethyl alcohol was distilled off under reduced pressure, and 28 mg of the isomerized ester was recovered.

EXAMPLE 9

200 mg of fenvalerate Aβ having the same composition as that of the fenvalerate Aβ used in Example 6 was dissolved in 200 mg of ethyl alcohol, and, as a catalyst, 20 mg of a base-type ion exchange resin (DOWEX 2×8, a trademark for a product of the Dow Chemical Company) was added. The mixture was maintained at 70° C. for 6 hours. Then, the solution was cooled to room temperature, and a sample of the solution was analyzed by gas chromatography. As to the alcohol moiety of the ester, 54.3% of the (R) isomer and 45.7% of the (S) isomer were found present.

The catalyst was separated by filtration, and the ethyl alcohol was distilled off under reduced pressure. Thus, 195 mg of the isomerized ester was recovered.

EXAMPLE 10

50 mg of fenvalerate Aβ having the same composition as that of the fenvalerate Aβ used in Example 6 was dissolved in 5 ml of methyl alcohol, and, as a catalyst, 5 mg of a base-type ion exchange resin (DOWEX 2×8) was added. The mixture was maintained at 60° C. for 6 hours. Thereafter, the solution was cooled to room temperature, and a sample of the solution was analyzed by gas chromatography. As to the alcohol moiety of the ester in the solution, 20.1% of the (S) isomer and 79.9% of the (R) isomer were found. The catalyst was separated by filtration, and the methyl alcohol was distilled off under reduced pressure. Thus, 48 mg of the isomerized ester was recovered.

EXAMPLE 11

100 mg of fenvalerate Aβ having the same composition as that of the fenvalerate Aβ used in Example 6 was dissolved in 100 mg of n-butanol, and, as a catalyst, 10 mg of a base-type ion exchange resin (DOWEX 2×8) was added. The mixture was maintained at 70° C. for 6 hours. Then, the solution was cooled to room temperature, and a sample of the solution was analyzed by gas chromatography. As to the alcohol moiety of the ester in the solution, 26.4% of the (S) isomer and 73.6% of the (R) isomer were found. The catalyst was separated by filtration, and the n-butanol was distilled off under reduced pressure. Thus, 94 mg of the isomerized ester was recovered.

EXAMPLE 12

300 mg of fenvalerate Aβ having the same composition as that of the fenvalerate Aβ used in Example 6 was dissolved in 300 mg of ethyl alcohol, and, as a catalyst, 30 mg of anhydrous potassium carbonate was added. The mixture was maintained at 70° C. for 6 hours. Then, the solution was cooled to room temperature, and a sample of the solution was analyzed by gas chromatography. As to the alcohol moiety of the ester in the solution, 55.1% of the (R) isomer and 44.9% of the (S) isomer were found. A 10% ethanol solution of acetic acid in an amount equal to that of the anhydrous potassium carbonate added to the solution was added to neutralize the solution. The ethyl alcohol was distilled off under reduced pressure, and the residue was dissolved in 20 ml of benzene. The solution was washed twice with 5 ml of water. The benzene layer was concentrated under reduced pressure, and 280 mg of the isomerized ester was recovered.

EXAMPLE 13

The procedures of Example 12 were repeated except that 30 mg of sodium hydrogen carbonate was used as a catalyst instead of the anhydrous potassium carbonate. A gas chromatographic analysis showed that the alcohol moiety of the ester comprised 68.0% of the (R) isomer and 32.0% of the (S) isomer. 288 mg of the isomerized ester was recovered.

EXAMPLE 14

210 mg of fenvalerate A$\beta$ having the same composition as that of the fenvalerate A$\beta$ used in Example 6 was dissolved in 1.90 g of ethyl alcohol. The solution was allowed to flow down over a period of time of 1.5 hours through a column packed with 25 ml of a base-type ion exchange resin (AMBERLITE IR-45, trade name for a product of the Rohm & Haas Company), as a catalyst, in ethanol. Fresh ethyl alcohol (70 ml) was further passed through the column over a period of time of 2.5 hours. The eluates were combined, analyzed by gas chromatography, and, as to the alcohol moiety of the ester, such was found to comprise 64.3% of the (R) isomer and 35.7% of the (S) isomer. The combined eluates were concentrated under reduced pressure, and 202 mg of the isomerized ester was recovered.

EXAMPLE 15

The procedures of Example 14 were repeated except that a solution of 108 mg of the ester in 10 g of ethyl alcohol was used. After isomerization, as to the alcohol moiety of the ester, the proportion of the (R) isomer was 56.2%, and that of the (S) isomer was 43.8%. 103 mg of the ester was recovered.

EXAMPLE 16

The procedures of Example 9 were repeated except that 20 mg of active alumina (for chromatography, a product of Wako Junyaku Co., Ltd.) was used as a catalyst instead of the base-type ion exchange resin. After isomerization, as to the alcohol moiety of the ester, the proportion of the (R) isomer was 61%, and that of the (S) isomer was 39%. 192 mg of the isomerized ester was recovered.

EXAMPLE 17

50 mg of fenvalerate A$\beta$ having the same composition as that of the fenvalerate A$\beta$ used in Example 6 was dissolved in 200 mg of a mixture of benzene and ethyl alcohol (9:1 by weight), and 5 mg of a base-type ion exchange resin (AMBERLITE IRA-93, trade name for a product of the Rohm & Haas Company) was added as a catalyst. The mixture was maintained at 70° C. for 6 hours. Thereafter, the solution was cooled to room temperature, and a sample of the solution was analyzed by gas chromatography. As to the alcohol moiety of the ester in the solution, 72.4% of the (R) isomer and 27.6% of the (S) isomer were found. The catalyst was separated by filtration, and the solvent was distilled off under reduced pressure. Thus, 47 mg of the isomerized ester was recovered.

EXAMPLE 18

104 mg of fenvalerate A$\beta$ having the same composition as that of the fenvalerate A$\beta$ used in Example 6 was dissolved in 0.94 g of ethyl alcohol, and the solution was allowed to flow down through a glass column packed with 20 ml of a base-type ion exchange resin (AMBERLITE IRA-93) in ethanol over a period of 10 minutes.

50 ml of fresh ethyl alcohol was passed through the column over a period of 2.5 hours. The eluates were combined, and analyzed by gas chromatography. The combined eluates were found to contain, as to the alcohol moiety of the ester present, 52.5% of the (R) isomer and 47.5% of the (S) isomer. The eluates were concentrated under reduced pressure, and 101 mg of the isomerized ester was recovered.

EXAMPLE 19

200 mg of fenvalerate A$\beta$ having the same composition as that of the fenvalerate A$\beta$ used in Example 6 was dissolved in 800 mg of benzene, and 20 mg of a base-type ion exchange resin (AMBERLIST A-21, a trade name for a product of the Rohm & Haas Company) was added as a catalyst. The mixture was maintained at 70° C. for 6 hours. Then, the solution was cooled to room temperature, and a sample of the solution was analyzed by gas chromatography. As to the alcohol moiety of the ester in the solution, 72.4% of the (R) isomer and 27.6% of the (S) isomer were found present. The catalyst was separated by filtration, and the benzene was distilled off under reduced pressure. Thus, 194 mg of the isomerized ester was recovered.

EXAMPLE 20

200 mg of fenvalerate A$\beta$ having the same composition as that of the fenvalerate A$\beta$ used in Example 6 was dissolved in 200 mg of ethyl acetate, and 20 mg of anhydrous potassium carbonate was added as a catalyst. The mixture was maintained at 60° C. for 6 hours. Then, the solution was cooled to room temperature, and a sample of the solution was analyzed by gas chromatography. The solution was found to contain, as to the alcohol moiety of the ester present, 85.5% of the (R) isomer and 14.5% of the (S) isomer. The catalyst was separated by filtration, and the ethyl acetate was distilled off under reduced pressure. Thus, 197 mg of the isomerized ester was recovered.

EXAMPLE 21

100 mg of fenvalerate A$\beta$ having the same composition as that of the fenvalerate A$\beta$ used in Example 6 was dissolved in 400 mg of ethyl acetate, and 10 mg of a base-type ion exchange resin (AMBERLITE IRA-93) was added as a catalyst. The mixture was maintained at 60° C. for 6 hours. Then, the solution was cooled to room temperature, and a sample of the solution was analyzed by gas chromatography. The solution was found to contain, as to the alcohol moiety of the ester present, 73.8% of the (R) isomer, and 26.2% of the (S) isomer. The catalyst was separated by filtration, and the ethyl acetate was distilled off under reduced pressure. Thus, 98 mg of the isomerized ester was recovered.

EXAMPLE 22

100 mg of fenvalerate Aβ having the same composition as that of the fenvalerate Aβ used in Example 6 was dissolved in 400 mg of n-hexane, and 10 mg of a strong base-type ion exchange resin (AMBERLIST A-27, OH-type, a trade name for a product of the Rohm & Haas Company) was added as a catalyst. The mixture was maintained at 60° C. for 6 hours. Then, the solution was cooled room temperature, and a sample of the solution was analyzed by gas chromatography. The solution was found to contain, as to the alcohol moiety of the ester present, 52.4% of the (R) isomer and 47.6% of the (S) isomer. The catalyst was separated by filtration, and the n-hexane was distilled off under reduced pressure. Thus, 94 mg of the isomerized ester was recovered.

EXAMPLE 23

50 mg of fenvalerate Aβ having the same composition as that of the fenvalerate Aβ used in Example 6 was dissolved in 200 mg of dichloromethane, and 5 mg of a strong base-type ion exchange resin (AMBERLIST A-27, OH type) was added as a catalyst. The mixture was maintained at 40° C. for 6 hours. Then, the solution was cooled to room temperature, and a sample of the solution was analyzed by gas chromatography. The solution was found to contain, as to the alcohol moiety of the ester present, 62.4% of the (R) isomer and 37.6% of the (S) isomer. The catalyst was separated by filtration, and the dichloromethane was distilled off under reduced pressure. Thus, 47 mg of the isomerized ester was recovered.

EXAMPLE 24

250 mg of fenvalerate Aβ having the same composition as that of the fenvalerate Aβ used in Example 6 was dissolved in 2.25 g of benzene, and the solution was allowed to flow down through a glass column packed with 25 ml of a strong base-type ion exchange resin (AMBERLIST A-27, OH type), as a catalyst, in benzene over a period of 2 hours. The column was eluted with 150 ml of fresh benzene over a period of 4 hours. The eluates were combined, and analyzed by gas chromatography. The product was found to contain, as to the alcohol moiety of the ester, 52.5% of the (R) isomer and 47.5% of the (S) isomer. The eluates were concentrated under reduced pressure, and 246 mg of the isomerized ester was recovered.

EXAMPLE 25

2.59 g of fenvalerate Aβ having the same composition as that of the fenvalerate Aβ used in Example 6 was dissolved in 5.2 g of ethanol, and 52 mg of triethylamine was added as a catalyst. The mixture was allowed to stand for 1 day at room temperature. Then, a sample of the solution was analyzed by gas chromatography, and the solution was found to contain, as to the alcohol moiety of the ester, 54.5% of the (R) isomer and 45.5% of the (S) isomer. The ethanol and triethylamine were distilled off under reduced pressure, and 2.52 g of the isomerized fanvalerate A was recovered.

EXAMPLE 26

To the filtrate obtained in Example 1 was added 0.35 g of a base-type ion exchange resin (DOWEX 2×8), as a catalyst, and the mixture was maintained at 70° C. for 6 hours. Then, the solution was cooled to room temperature, and a sample of the solution was analyzed by gas chromatography. The solution was found to contain, as to the alcohol moiety of the ester, 51.8% of the (R) isomer and 48.2% of the (S) isomer. The catalyst was separated by filtration, and the ethyl alcohol was distilled off under reduced pressure until the total weight of the solution reached 7.5 g. To the concentrate was added 1 mg of a crystal of fenvalerate Aα as a seed, and the mixture was allowed to stand at −5° C. for 3 days. Then, the precipitated crystals were collected by filtration. The solid deposited on the filter was washed three times with 0.5 g of cold ethyl alcohol (0°–5° C.).

The yield of the crystals was 0.46 g. A gas chromatographic analysis of the crystals showed, as to the alcohol moiety of the esters, 3.9% of the (R) isomer and 96.1% of the (S) isomer.

EXAMPLE 27

An ethyl alcohol solution of the ester having the composition as described in Example 26 (concentration 10%; total amount of the solution 30 g) was allowed to flow down through a glass column packed with 100 ml of a base-type ion exchange resin (AMBERLITE IR-45), as a catalyst, in ethanol over a period of 5 hours. The column was eluted with 30 g of fresh ethyl alcohol over a period of 3 hours.

The eluates were combined, and a sample of the combined eluates was analyzed by gas chromatography. The combined eluates were found to contain, as to the alcohol moiety of the ester, 55.3% of the (R) isomer and 44.7% of the (S) isomer.

The eluates were concentrated under reduced pressure until the total weight of the solution reached 10 g. To the concentrate was added 4.2 g of fresh fenvalerate A, and the mixture was heated to thereby dissolve the fenvalerate A. The resulting solution was cooled to room temperature. 10 mg of a crystal of fenvalerate Aα was added as a seed. The mixture was allowed to stand at −6° C. for 2 days. Then, the precipitated crystals were collected by filtration. The solid deposited on the filter was washed twice with 1.0 g of cold ethanol (0°–5° C.). The yield of the crystals was 1.02 g, and, as to the alcohol moiety of the ester, 3.9% of the (R) isomer and 96.1% of the (S) isomer were found.

EXAMPLE 28

5.0 g of fenvalerate A was dissovled in 5.5 g of a mixture of benzene and n-hexane (1:5 by weight), and 1 mg of a crystal of fenvalerate Aα was added as a seed. The mixture was allowed to stand at −6° C. for 4 days. Then, the precipitated crystals were collected by filtration. The solid deposited on the filter was washed three times with 2 ml of cold n-hexane. The yield of the crystals was 0.62 g. It was found on analysis of the crystals that, as to the alcohol moiety of the ester, 2.7% of the (R) isomer and 97.3% of the (S) isomer were present. To the filtrate was added 0.35 g of a strong base-type ion exchange resin (AMBERLIST A-27, OH type), as a catalyst, and the mixture was maintained at 60° C. for 6 hours. Thereafter, the solution was cooled to room temperature, and a sample of the solution was analyzed by gas chromatography. It was found that, as to the alcohol moiety of the ester, 52.8% of the (R) isomer and 47.2% of the (S) isomer were present. The catalyst was separated by filtration, and the solvent was distilled off under reduced pressure until the total weight of the solution reached 10 g. To the concentrate was added 1 mg of fenvalerate Aα as a seed, and the mixture was allowed to stand at −5° C. for 3 days. Then, the precipitated crystals were collected by filtration. The solid deposited on the filter was washed three times with 0.5 g of cold hexane (0–5° C.). The yield of the crystals was 0.28 g. On analysis of the crystals, as to the alcohol moiety of the ester, 3.9% of the (R) isomer and 96.1% of the (S) isomer were found present.

EXAMPLE 29

A solution of an ester having the same composition as the first filtrate in Example 28 in a mixture of benzene and n-hexane (concentration 10%, total amount of the solution: 30 g) was allowed to flow down through a glass column packed with 100 ml of a strong base-type ion exchange resin (AMBERLIST A-27, OH type), as a catalyst, in benzene over a period of 5 hours. The column was eluted with 30 g of fresh benzene over a period of 3 hours.

The eluates were combined, and a sample of the combined eluates was analyzed by gas chromatography. It was found, as to the alcohol moiety of the ester, 53.3% of the (R) isomer and 46.7% of the (S) isomer were present. The solvent was distilled off under reduced pressure from the combined eluates, and 3.5 g of a mixture of benzene and n-hexane (1:5 by weight) was added to the residue. The mixture was heated to 40° C. to thereby dissolve the residue in the benzene-n-hexane mixture. The resulting solution was cooled to room temperature, and 10 mg of a crystal of fenvalerate A$\alpha$ was added as a seed. The mixture was allowed to stand for 4 days at $-6°$ C. Then, the precipitated crystals were collected by filtration. The solid deposited on the filter was washed twice with 1.0 g of cold hexane (0°–5° C.). The yield of the crystals was 0.35 g. On analysis of the crystals, as to the alcohol moiety of the ester, 3.9% of the (R) isomer and 96.1% of the (S) isomer were found present.

EXAMPLE 30

5.82 g of fenvalerate A was dissolved in 11.6 g of methanol, and 1 mg of a crystal of fenvalerate A$\alpha$ was added as a seed. Further, 120 mg of triethylamine was added as a catalyst, and the mixture was stirred at 2° to 4° C. for 2 days. Then, the precipitated crystals were collected by filtration. The solid deposited on the filter was washed twice with 5 ml of cold hexane (0°–5° C.). The yield of the crystals was 4.61 g (79.3% by weight based on the fenvalerate A used). On analysis of the crystals, as to the alcohol moiety of the ester, 1.4% of the (R) isomer and 98.6% of the (S) isomer were found present. As to the alcohol moiety of the fenvalerate A recovered from the filtrate, 51.0% of the (R) isomer and 49.9% of the (S) isomer were found present.

EXAMPLE 31

6.78 g of fenvalerate A was dissolved in 6.8 g of methanol, and 1 mg of a crystal of fenvalerate A$\alpha$ was added as a seed. Further, 68 mg of triethylamine was added as a catalyst, and the mixture was stirred at 2° to 4° C. for 1 day. Then, the precipitated crystals were collected by filtration. The solid deposited on the filter was washed twice with 5 ml of cold hexane (0°–5° C.). The yield of the crystals was 5.91 g (87.2% by weight based on the fenvalerate A used). On analysis of the crystals, as to the alcohol moiety of the ester, 2.0% of the (R) isomer and 98.0% of the (S) isomer were found.

EXAMPLE 32

7.22 g of fenvalerate A was dissolved in 7.2 g of methanol, and 1 mg of a crystal of fenvalerate A$\alpha$ was added as a seed. Further, 43 mg of n-propylamine was added as a catalyst, and the mixture was stirred at 2° to 4° C. for one day. Then, the precipitated crystals were collected by filtration, and the solid deposited on the filter was washed twice with 5 ml of cold hexane (0°–5° C.). The yield of the crystals was 5.57 g (77.2% by weight based on the fenvalerate A used). On analysis of the crystals, as to the alcohol moiety of the ester, 4.4% of the (R) isomer and 95.6% of the (S) isomer were found.

EXAMPLE 33

6.49 g of fenvalerate A was dissolved in 6.5 g of methanol, and 1 mg of a crystal of fenvalerate A$\alpha$ was added as a seed. Further, 47 mg of diethylamine was added as a catalyst, and the mixture was stirred at 2° to 4° C. for 1 day. Thereafter, the precipitated crystals were collected by filtration, and the solid deposited on the filter was washed twice with 5 ml of cold hexane (0°–5° l C.). The yield of the crystals was 4.84 g (74.6% by weight based on the fenvalerate A used). On analysis of the crystals, as to the alcohol moiety of the ester, 2.3% of the (R) isomer and 97.7% of the (S) isomer were found.

EXAMPLE 34

7.36 g of fenvalerate A was dissolved in 7.4 g of ethanol, and 1 mg of a crystal of fenvalerate A$\alpha$ was added as a seed. Further, 74 mg of triethylamine was added as a catalyst, and the mixture was stirred at 2° to 4° C. for 1 day. Then, the precipitated crystals were collected by filtration. The solid deposited on the filter was washed twice with 3 ml of cold hexane (0°–5° C.). The yield of the crystals was 3.04 g (41.3% by weight based on the fenvalerate A used). On analysis of the crystals, as to the alcohol moiety of the ester, 4.0% of the (R) isomer and 96.0% of the (S) isomer were found.

EXAMPLE 35

7.70 g of fenvalerate A was dissolved in 7.7 g of methanol, and 1 mg of a crystal of fenvalerate A$\alpha$ was added as a seed. Further, 200 mg of triphenyl phosphine was added as a catalyst, and the mixture was stirred at 2° to 4° C. for 1 day. Then, the precipitated crystals were collected by filtration. The solid deposited on the filter was washed twice with 3 ml of cold hexane (0°–5° C.). The yield of the crystals was 3.60 g (46.8% by weight based on the fenvalerate A used). On analysis of the crystals, the alcohol moiety of the ester was found to comprise 3.4% of the (R) isomer and 96.6% of the (S) isomer.

EXAMPLE 36

6.64 g of fenvalerate A was dissolved in 6.6 g of methanol, and 1 mg of a crystal of fenvalerate A$\alpha$ was added as a seed. Further, 62 mg of aniline was added as a catalyst, and the mixture was stirred at 2° to 4° for 1 day. Then, the precipitated crystals were collected by filtration. The solid deposited on the filter was washed twice with cold hexane (0°–5° C.) The yield of the crystals was 2.99 g (45.1% by weight based on the fenvalerate A used). On analysis of the crystals, the alcohol moiety of the ester was found to comprise 2.9% of the (R) isomer and 97.1% of the (S) isomer.

EXAMPLE 37

7.85 g of fenvalerate A was dissolved in 7.2 g of methanol, and 1 mg of a crystal of fenvalerate Aα was added as a seed. Further, 0.71 g of a 10% methanol solution of tetramethyl ammonium hydroxide as a catalyst was added, and the mixture was stirred at 2° to 4° C. for 1 day. Then, the precipitated crystals were collected by filtration. The solid deposited on the filter was washed twice with 3 ml of cold hexane (0°-5° C.). The yield of the crystals was 4.05 g (51.6% by weight based on the fenvalerate A used). On analysis of the crystals, the alcohol moiety of the ester was found to comprise 3.8% of the (R) isomer and 96.2% of the (S) isomer.

EXAMPLE 38

40.00 g of fenvalerate A was dissolved in 80 g of methanol, and 1 mg of a crystal of fenvalerate Aα was added as a seed. Further, 2.00 g of triethylamine was added as a catalyst, and the mixture was stirred at −6° C. for 1 day. Then, the precipitated crystals were collected by filtration, and the solid deposited on the filter was washed twice with 20 ml of cold methanol (0°-5° C.). The yield of the crystals was 33.36 g (83.4% by weight based on the fenvalerate A used). On analysis of the crystals, the alcohol moiety of the ester was found to comprise 2.3% of the (R) isomer and 97.7% of the (S) isomer.

EXAMPLE 39

40.00 g of fenvalerate A was dissolved in 40 g of methanol, and 1 mg of a crystal of fenvalerate Aα was added as a seed. Further, 0.40 g of triethylamine was added as a catalyst, and the mixture was stirred at −6° C. for 3 days. Then, the precipitated crystals were collected by filtration. The solid deposited on the filter was washed twice with 20 ml of cold methanol (0°-5° C.). The yield of the crystals was 35.82 g (89.6% by weight based on the fenvalerate A used). On analysis of the crystals, the alcohol moiety of the ester was found to comprise 2.5% of the (R) isomer and 97.5% of the (S) isomer.

EXAMPLE 40

10.00 g of fenvalerate A was dissolved in 10 g of methanol, and 1 mg of a crystal of fenvalerate Aα was added as a seed. Furthermore, 0.10 g of pyridine was added as a catalyst, and the mixture was stirred at −6° C. for 1 day. Then, the precipitated crystals were collected by filtration. The solid deposited on the filter was washed twice with 5 ml of cold methanol (0°-5° C.). The yield of the crystals was 4.36 g (43.6% by weight based on the fenvalerate A used). On analysis of the crystals, the alcohol moiety of the ester was found to comprise 3.0% of the (R) isomer and 97.0% of the (S) isomer.

EXAMPLE 41

10.00 g of fenvalerate A was dissolved in 20 g of methanol, and 1 mg of a crystal of fenvalerate Aα was added as a seed. Further, 0.20 g of a 40% aqueous solution of methylamine, as a catalyst, was added, and the mixture was stirred at −6° C. for 1 day. Then, the precipitated crystals were collected by filtration. The solid deposited on the filter was washed twice with 5 ml of cold methanol (0°-5° C.). The yield of the crystals was 8.52 g (85.2% based on the fenvalerate A used). On analysis of the crystals, the alcohol moiety of the ester was found to comprise 2.3% of the (R) isomer and 97.7% of the (S) isomer.

EXAMPLE 42

40.00 g of fenvalerate A was dissolved in 80 g of methanol, and 1 mg of a crystal of fenvalerate Aα was added as a seed. Furthermore, 0.48 g of a 28% aqueous ammonia solution was added as a catalyst, and the mixture was stirred at −6° C. for 1 day. Then, the precipitated crystals were collected by filtration. The solid deposited on the filter was washed twice with 20 ml of cold methanol (0°-5° C.). The yield of the crystals was 33.20 g (83.0% by weight based on the fenvalerate A used). On analysis of the crystals, the alcohol moiety of the ester was found to comprise 2.3% of the (R) isomer and 97.7% of the (S) isomer.

EXAMPLE 43

10.00 g of fenvalerate A was dissolved in 10 g of methanol, and 1 mg of a crystal of fenvalerate Aα was added as a seed. Further, 0.10 g of ethylenediamine was added as a catalyst, and the mixture was stirred at −6° C. for 1 day. Then, the precipitated crystals were collected by filtration. The solid deposited on the filter was washed twice with 5 ml of cold methanol (0°-5° C.). The yield of the crystals was 8.12 g (81.2% by weight based on the fenvalerate A used). On analysis of the crystals, the alcohol moiety of the ester was found to comprise 2.6% of the (R) isomer and 97.4% of the (S) isomer.

EXAMPLE 44

100.00 g of fenvalerate A was dissolved in 200 g of methanol, and 1 mg of a crystal of fenvalerate Aα was added as a seed. Further, 3.00 g of triethylamine was added as a catalyst, and the mixture was stirred at −13° C. for 1 day. Then, the precipitated crystals were collected by filtration. The solid deposited on the filter was washed twice with 50 ml of cold methanol (0°-5° C.). The yield of the crystals was 84.21 g (84.2% by weight based on the fenvalerate A used). On analysis of the crystals, the alcohol moiety of the ester was found to comprise 3.0% of the (R) isomer and 97.0% of the (S) isomer.

EXAMPLE 45

10.00 g of fenvalerate A was dissolved in 10 g of methanol, and 1 mg of a crystal of fenvalerate Aα was added as a seed. Further, 0.10 g of triethylamine was added as a catalyst, and the mixture was stirred at 12° C. for 1 day. Then, the precipitated crystals were collected by filtration. The solid deposited on the filter was washed twice with 5 ml of cold methanol (0°-5° C.). The yield of the crystals was 7.43 g (74.3% by weight based on the fenvalerate A used). On analysis of the crystals, the alcohol moiety of the ester was found to comprise 1.2% of the (R) isomer and 98.8% of the (S) isomer.

EXAMPLE 46

40.00 g of fenvalerate A was dissolved in 60 g of methanol, and 10 mg of a crystal of fenvalerate Aα was added as a seed. Further, 1.95 g of methanol having ammonia dissolved therein (ammonia content: 8.3% by weight) was added as a catalyst, and the mixture was stirred at −6° C. for 1 day. Then, the precipitated crystals were collected by filtration. The solid deposited on the filter was washed twice with 20 ml of cold methanol (0°-5° C.). The yield of the crystals was 34.56 g (86.4% by weight based on the fenvalerate A used). On analysis of the crystals, the alcohol moiety of the ester was found to comprise 2.3% of the (R) isomer and 97.7% of the (S) isomer.

EXAMPLE 47

40.00 g of fenvalerate A was dissolved in 80 g of methylcyclohexane, and 10 mg of a crystal of fenvalerate Aα was added as a seed. Further, 9.8 of methanol having ammonia dissolved therein (ammonia content: 8.3% by weight) was added as a catalyst, and the mixture was stirred at −6° C. for 1 day. Then, the precipitated crystals were collected by filtration. The solid deposited on the filter was washed twice with 20 ml of cold methylcyclohexane (0°-5° C.). The yield of the crystals was 31.40 g (78.5% by weight based on the fenvalerate A used). On analysis of the crystals, the alcohol moiety of the ester was found to comprise 1.4% of the (R) isomer and 98.6% of the (S) isomer.

EXAMPLE 48

40.00 g of fenvalerate A was dissolved in a mixture of 10 g of toluene and 70 g of heptane, and 10 mg of a crystal of fenvalerate Aα was added as a seed. Further, 9.8 g of methanol having ammonia dissolved therein (ammonia content: 8.3% by weight) was added as a catalyst, and the mixture was stirred at −6° C. for 1 day. Then, the precipitated crystals were collected by filtration. The solid deposited on the filter was washed twice with 20 ml of cold heptane (0°-5° C.). The yield of the crystals was 31.72 g (79.3% by weight based on the fenvalerate A used). On analysis of the crystals, the alcohol moiety of the ester was found to comprise 2.2% of the (R) isomer and 97.8% of the (S) isomer.

EXAMPLE 49

40.00 g of fenvalerate A was dissolved in 60 g of methanol, and 10 mg of a crystal of fenvalerate Aα was added as a seed. Further, a solution of 38 mg of sodium hydroxide, as a catalyst, dissolved in 1 g of methanol was added, and the mixture was stirred at −6° C. for 1 day. Then, the precipitated crystals were collected by filtration. The solid deposited on the filter was washed twice with 20 ml of cold methanol (0°-5° C.). The yield of the crystals was 23.84 g (59.6% by weight based on the fenvalerate A used). On analysis of the crystals, the alcohol moiety of the ester was found to comprise 2.8% of the (R) isomer and 97.2% of the (S) isomer.

EXAMPLE 50

40.00 g of fenvalerate A was dissolved in 60 g of methanol, and 10 mg of a crystal of fenvalerate Aα was added. Further, a solution of 47 mg of sodium cyanide, as a catalyst, dissolved in 2 g of methanol was added, and the mixture was stirred at −6° C. for 1 day. Then, the precipitated crystals were collected by filtration. The solid deposited on the filter was washed twice with 20 ml of cold methanol (0°-5° C.). The yield of the crystals was 22.8 g (57.2% by weight based on the fenvalerate A used). On analysis of the crystals, the alcohol moiety of the ester was found to comprise 2.2% of the (R) isomer and 97.8% of the (S) isomer.

EXAMPLE 51

40.00 g of fenvalerate A (in which the alcohol moiety had a composition of 51.0% of a peak ascribable to the (R) isomer and 49.0% of a peak ascribable to the (S) isomer and the acid moiety had an optical purity of 82.0%) was dissolved in 60 g of methanol, and 10 mg of a crystal of fenvalerate Aα was added as a seed. Further, 0.8 g of triethylamine was added as a catalyst, and the mixture was stirred at −6° for 1 day. Then, the precipitated crystals were collected by filtration. The solid deposited on the filter was washed twice with 20 ml of cold methanol (0°-5° C.). The yield of the crystals was 21.36 g (53.4% by weight based on the fenvalerate A used). On analysis of the crystals, the alcohol moiety of the ester was found to comprise 2.5% of the (R) isomer and 97.5% of the (S) isomer.

EXAMPLE 52

40.00 g of fenvalerate A was dissolved in 60 g of methanol, and 10 mg of a crystal of fenvalerate Aα was added as a seed. Further, 0.8 g of triethylamine was added as a catalyst, and the mixture was stirred at −6° C. for 1 day. Then, the reaction mixture was added to 50 ml of a 1% hydrochloric acid aqueous solution and 50 ml of toluene, and the mixture was fractionated. The thus-obtained aqueous layer was extracted with 50 ml of toluene. The toluene layers were combined, and washed twice with 50 ml of water. The toluene was distilled off under reduced pressure, and fenvalerate Aα-rich fenvalerate A was obtained as a pale yellow oily substance. The yield was 39.73 g (99.3% of the theoretical amount). On analysis of the oil, the alcohol moiety of the ester was found to comprise 7.7% of the (R) isomer and 92.3% of the (S) isomer.

EXAMPLE 53

The same procedures as those described in Example 38 above were repeated. One day later, about 10% of the slurry was added into a solution of fenvalerate A composed of 400 g of fenvalerate A and 600 g of methanol, which was cooled at −6° C. Further, 8.0 g of triethylamine was added as a catalyst, and the mixture was stirred at −6° C. for 1 day. Then, the precipitated crystals were collected by filtration, and the solid deposited on the filter was washed twice with 200 ml of cold methanol (0°-5° C.). The yield of the crystals was 381.9 g (86.8% by weight based on the fenvalerate A used). On analysis of the crystals, the alcohol moiety of the ester was found to comprise 2.4% of the (R) isomer and 97.6% of the (S) isomer.

EXAMPLE 54

40.00 g of fenvalerate A was dissolved in 60 g of methanol, and 10 mg of a crystal of fenvalerate Aα was added as a seed. Further, 0.12 g of 1,5-diazabicyclo[4, 3, 0]non-5-ene was added, and the mixture was stirred at −6° C. for 1 day. Then, the precipitated crystals were collected by filtration, and the solid deposited on the filter was washed twice with 20 ml of cold methanol (0°-5° C.). The yield of the crystals was 32.35 g (80.9% by weight based on the fenvalerate A used). On analysis of the crystals, the alcohol moiety of the ester was found to comprise 3.2% of the (R) isomer and 96.8% of the (S) isomer.

EXAMPLE 55

40.00 g of fenvalerate A was dissolved in the mixed solvent of 5 g of toluene, 35 g of heptane and 20 g of methanol. 10 mg of a crystal of fenvalerate Aα and 4.8 g of triethylamine were added, and the mixture was stirred at −6° C. for 1 day. Then, the precipitated crystals were collected by filtration, and the solid deposited on the filter was washed twice with 20 ml of cold methanol (0°–5° C.). The yield of the crystals was 23.72 g (59.3% by weight based on the fenvalerate A used). On analysis of the crystals, the alcohol moiety of the ester was found to comprise 1.6% of the (R) isomer and 98.4% of the (S) isomer.

EXAMPLE 56

40.00 g of fenvalerate A was dissolved in 60 g of methanol, and 10 mg of a crystal of fenvalerate Aα was added as a seed. Further, a solution of 38 mg of sodium hydroxide dissolved in 1 g of methanol was added, and the mixture was stirred at −6° C. for 1 day. Then, the reaction mixture was added to 50 ml of a 1% hydrochloric acid aqueous solution and 50 ml of toluene, and the mixture was fractionated. The thus-obtained aqueous layer was extracted with 50 ml of toluene. The toluene layers were combined, and washed twice with 50 ml of water. The toluene was distilled off under reduced pressure, and fenvalerate Aα-rich fenvalerate A was obtained as a pale yellow oily substance. The yield was 39.61 g (99.0% of the theoretical amount). On analysis of the oil, the alcohol moiety of the ester was found to comprise 10.8% of the (R) isomer and 89.2% of the (S) isomer.

While the invention has been described in detail and with reference to specific embodiments thereof, it will be apparent to one skilled in the art that various changes and modifications can be made therein without departing from the spirit and scope thereof.

What is claimed is:

1. A process for preparing (S)-α-cyano-3-phenoxybenzyl (S)-2-(4-chlorophenyl)isovalerate, which comprises adding a seed crystal of (S)-α-cyano-3-phenoxybenzyl (S)-2-(4-chlorophenyl)isovalerate, (R)-α-cyano-3-phenoxybenzyl (R)-2-(4-chlorophenyl)isovalerate, or a mixture thereof, to a solution of (R, S)-α-cyano-3-phenoxybenzyl (S)-2-(4-chlorophenyl)isovalerate in a solvent in which (R)-α-cyano-3-phenoxybenzyl (S)-2-(4-chlorophenyl)isovalerate is soluble and (S)-α-cyano-3-phenoxybenzyl (S)-2-(4-chlorophenyl)isovalerate is substantially insoluble or soluble to a small extent, crystallizing (S)-α-cyano-3-phenoxybenzyl (S)-2-(4-chlorophenyl)isovalerate from the solution, and separating the crystalline (S)-α-cyano-3-phenoxybenzyl (S)-2-(4-chlorophenyl)isovalerate from the mother liquor.

2. The process of claim 1, wherein the solution of the (R, S)-α-cyano-3-phenoxybenzyl (S)-2-(4-chlorophenyl)isovalerate comprises a solution of (R, S)-α-cyano-3-phenoxybenzyl (S)-2-(4-chlorophenyl)isovalerate in a solvent of a lower alcohol with an aromatic hydrocarbon.

3. The process of claim 1, wherein the solution of the (R, S)-α-cyano-3-phenoxybenzyl (S)-2-(4-chlorophenyl)isovalerate comprises a solution of (R, S)-α-cyano-3-phenoxylbenzyl (S)-2-(4-chlorophenyl)isovalerate in an aliphatic hydrocarbon, an alicyclic hydrocarbon, or a mixed solvent of an aliphatic hydrocarbon and/or an alicyclic hydrocarbon with an aromatic hydrocarbon and/or a lower alcohol.

4. A process for isomerizing optically active α-cyano-3-phenoxybenzyl 2-(4-chlorophenyl)isovalerate at the asymmetric carbon atom of the 3-phenoxybenzyl moiety, which comprises isomerizing the optically active α-cyano-3-phenoxy-benzyl 2-(4-chlorophenyl)isovalerate in a protonic solvent or a mixed solvent of a protonic solvent with an aprotic solvent.

5. The process of claim 4, wherein the protonic solvent is a lower alcohol.

6. A process for isomerizing optically active α-cyano-3-phenoxybenzyl 2-(4-chlorophenyl)isovalerate at the asymmetric carbon atom of the 3-phenoxybenzyl moiety, which comprises isomerizing the optically active α-cyano-3-phenoxybenzyl 2-(4-chlorophenyl)isovalerate in a solvent in which said optically active isomer of α-cyano-3-phenoxybenzyl 2-(4-chlorophenyl) isovalerate is soluble, in the presence of a basic substance as a catalyst chosen from the group consisting of ammonia, a primary amine, a secondary amine, a tertiary amine, a quaternary ammonium hydroxide, sodium hydroxide, potassium hydroxide and a base-type ion exchange resin.

7. The process of claim 6, wherein the basic substance is substantially insoluble in the solvent used.

8. The process of claim 6, wherein the basic substance is a base-type ion exchange resin.

9. The process of claim 6, 7 or 8, wherein the process comprises passing the solution of the optically active α-cyano-3-phenoxybenzyl 2-(4-chlorophenyl)isovalerate through a column packed with the basic substance.

10. The process of claim 1, 2 or 3, wherein the starting material is obtained by crystallizing (S)-α-cyano-3-phenoxybenzyl (S)-2-(4-chlorophenyl)isovalerate from a solution of (R, S)-α-cyano-3-phenoxybenzyl (S)-2-(4-chlorophenyl)isovalerate, in a solvent which can dissolve (R)-α-cyano-3-phenoxybenzyl (S)-2-(4-chlorophenyl)isovalerate but which dissolves (S)-α-cyano-3-phenoxybenzyl (S)-2-(4-chlorophenyl)isovalerate to only a small extent, separating the crystalline (S)-α-cyano-3-phenoxybenzyl (S)-2-(4-chlorophenyl)isovalerate from the mother liquor, and isomerizing the ester contained in the mother liquor in a protonic solvent or a mixed solvent of a protonic solvent with an aprotic solvent.

11. The process of claim 10, wherein the protonic solvent for the isomerization is a lower alcohol or a mixed solvent of a lower alcohol with an aliphatic hydrocarbon, an alicyclic hydrocarbon, an aromatic hydrocarbon, a halogenated hydrocarbon or an aprotic polar solvent.

12. The process of claim 10, wherein the protonic solvent for the isomerization is a lower alcohol.

13. The process of claim 1, 2 or 3, wherein the starting material is obtained by crystallizing (s)-α-cyano-3-phenoxybenzyl (S)-2-(4-chlorophenyl)isovalerate from a solution of (R, S)-α-cyano-3phenoxybenzyl (S)-2-(4-chlorophenyl)isovalerate in a solvent in which (R)-α-cyano3-phenoxybenzyl (S)-2-(4-chlorophenyl)isovalerate is soluble and (S)-α-cyano-3-phenoxybenzyl (S)-2-(4-chlorophenyl)isovalerate is substantially insoluble or soluble to a small extent, separating the crystalline (S)-α-cyano-3-phenoxybenzyl (S)-2-(4-chlorophenyl)isovalerate from the mother liquor, and isomerizing the ester contained in the mother liquor in a solvent in which said optical isomers of α-cyano-3-phenoxybenzyl 2-(4-chlorophenyl)isovalerate are soluble, in the presence of a basic substance as a catalyst chosen from the group consisting of ammonia, a primary amine, a secondary amine, a tertiary amine, a quaternary ammonium hydroxide, sodium hydroxide, potassium hydroxide and a base-type ion exchange resin.

14. The process of claim 13, wherein the basic substance used as a catalyst in the isomerization is a basic substance which is substantially insoluble in the solvent used for the solution.

15. The process of claim 14, wherein the basic catalyst is a base-type ion exchange resin.

16. The process of claim 14, wherein the isomerization is carried out by passing the solution through a column packed with the basic substance.

17. The process of claim 13, wherein the solvent for the isomerization is a lower alcohol or a mixed solvent of a lower alcohol with an aliphatic hydrocarbon, an alicyclic hydrocarbon, an aromatic hydrocarbon, a halogenated hydrocarbon or an aprotic polar solvent.

18. The process of claim 13, wherein the solvent for the isomerization is a lower alcohol.

19. The process of claim 13, wherein the solvent for the isomerization is an aliphatic hydrocarbon, an alicyclic hydrocarbon, or a mixed solvent of an aliphatic hydrocarbon or an alicyclic hydrocarbon with an aromatic hydrocarbon and/or a lower alcohol.

20. A process for preparing (S)-α-cyano-3-phenoxybenzyl (S)-2(4-chlorophenyl)isovalerate, which comprises crystallizing (S)-α-cyano-3-phenoxybenzyl (S)-2-(4-chlorophenyl)isovalerate from a solution of (R, S)-α-cyano-3-phenoxybenzyl (S)-2-(4-chlorophenyl)isovalerate in a solvent in which (S)-α-cyano-3-phenoxybenzyl (S)-2-(4-chlorophenyl)isovalerate is soluble only to a small extent and (R)-α-cyano-3-phenoxybenzyl (S)-2-(4-chlorophenyl)isovalerate is soluble, in the presence of a basic substance as a catalyst.

21. The process of claim 20, wherein the solvent is methanol, ethanol, or a mixed solvent of methanol with ethanol.

22. The process of claim 20, wherein the solvent is methanol.

23. The process of claim 20, wherein the solvent is an aliphatic hydrocarbon, an alicyclic hydrocarbon, a mixture of an aliphatic hydrocarbon and an aromatic hydrocarbon, or a mixture of an alicyclic hydrocarbon and an aromatic hydrocarbon.

24. The process of claim 20, wherein the solvent is a member selected from the group consisting of pentane, hexane and heptane.

25. The process of claim 20, wherein the solvent is a mixture of (a) a solvent selected from the group consisting of pentane, hexane and heptane and (b) a solvent selected from the group consisting of benzene, toluene and xylene.

26. The process of claim 20, wherein the solvent is a member selected from the group consisting of cyclohexane and methylcyclohexane.

27. The process of claim 20, 21, 22, 23, 24, 25 or 26, wherein the basic substance is a nitrogen-containing base or a phosphorous-containing base.

28. The process of claim 20, 21, 22, 23, 24, 25 or 26, wherein the basic substance is ammonia or an organic amine.

29. The process of claim 20, 21, 22, 23, 24, 25 or 26, wherein the basic substance is a member selected from the group consisting of an alkali metal hydroxide, an alkaline earth metal hydroxide, an alkali metal alcoholate, an alkaline earth metal alcoholate, an alkali metal amide, an alkaline earth metal amide, an alkali metal hydride, an alkaline earth metal hydride, and a base-type ion exchange resin.

30. The process of claim 29, wherein the basic substance is a member selected from the group consisting of an alkali metal hydroxide and an alkaline earth metal hydroxide.

31. A process for preparing (R, S)-α-cyano-3-phenoxybenzyl (S)-2-(4-chlorophenyl)isovalerate containing a major proportion of (S)-α-cyano-3-phenoxybenzyl (S)-2-(4-chlorophenyl)isovalerate, which comprises crystallizing (S)-α-cyano-3-phenoxybenzyl (S)-2-(4-chlorophenyl)isovalerate from solution of (R, S)-α-cyano-3-phenoxybenzyl (S)-2-(4-chlorophenyl)isovalerate in a solvent in which (S)-α-cyano-3-phenoxybenzyl (S)-2-(4-chlorophenyl)isovalerate is substantially insoluble or soluble to a small extent and (R)-α-cyano-3-phenoxybenzyl (S)-2-(4-chlorophenyl)isovalerate is soluble, in the presence of a basic substance as a catalyst to increase the proportion of (S)-α-cyano-3-phenoxybenzyl (S)-2-(4-chlorophenyl)isovalerate in the slurry, and recovering the resulting crystallization product together with (R, S)-α-cyano-3-phenoxybenzyl (S)-2-(4-chlorophenyl)isovalerate in the mother liquor.

32. The process of claim 31, wherein the solvent is methanol, ethanol, or a mixed solvent of methanol with ethanol.

33. The process of claim 31, wherein the solvent is methanol.

34. The process of claim 31, wherein the solvent is an aliphatic hydrocarbon, an alicyclic hydrocarbon, a mixture of an aliphatic hydrocarbon and an aromatic hydrocarbon, or a mixture of an alicyclic hydrocarbon and an aromatic hydrocarbon.

35. The process of claim 31, wherein the solvent is selected from the group consisting of pentane, hexane and heptane.

36. The process of claim 31, wherein the solvent is a mixture of (a) a solvent selected from the group consisting of pentane, hexane and heptane and (b) a solvent selected from the group consisting of benzene, toluene and xylene.

37. The process of claim 31, wherein the solvent is selected from the group consisting of cyclohexane, methylcyclohexane, and a mixed solvent containing cyclohexane or methylcyclohexane.

38. The process of claim 31, 32, 33, 34, 35, 36 or 37, wherein the basic substance used as a catalyst is a nitrogen-containing base or a phosphorus-containing base.

39. The process of claim 31, 32, 33, 34, 35, 36 or 37, wherein the basic substance used as a catalyst is ammonia or an organic amine.

40. The process of claim 31, 32, 33, 34, 35, 36 or 37, wherein the basic substance used as a catalyst is selected from the group consisting of an alkali metal hydroxide, an alkaline earth metal hydroxide, an alkali metal alcoholate, an alkaline earth metal alcoholate, an alkali metal amide, an alkaline earth metal amide, an alkali metal hydride, an alkaline earth metal hydride and a base-type ion exchange resin.

41. The process of claim 40, wherein the basic substance is selected from the group consisting of an alkali metal hydroxide and an alkaline earth metal hydroxide.

42. The process of claim 31, 32, 33, 34, 35, 36 or 37, wherein the process includes removing the basic substance after the crystallization.

43. The process of claim 31, 32, 33, 34, 35, 36 or 37, wherein the process includes neutralizing the basic substance with an acidic substance after the crystallization.

44. The process of claim 20, wherein the solvent is a mixed solvent of a lower alcohol selected from the group consisting of methanol and ethanol with an aliphatic hydrocarbon or an alicyclic hydrocarbon and/or an aromatic hydrocarbon.

45. The process of claim 44, wherein the lower alcohol is methanol.

46. The process of claim 44, wherein the aliphatic hydrocarbon is a member selected from the group consisting of pentane, hexane and heptane; the alicyclic hydrocarbon is a member selected from the group consisting of cyclohexane and methylcyclohexane; and the aromatic hydrocarbon is a member selected from the group consisting of benzene, toluene and xylene.

47. The process of claim 44, 45, or 46, wherein the basic substance is a nitrogen-containing base or a phosphorus-containing base.

48. The process of claim 44, 45 or 46, wherein the basic substance is ammonia or an organic amine.

49. The process of claim 44, 45 or 46, wherein the basic substance is a member selected from the group consisting of an alkali metal hydroxide, an alkaline earth metal hydroxide, an alkali metal alcoholate, an alkaline earth metal alcoholate, an alkali metal amide, an alkaline earth metal amide, an alkali metal hydride, an alkaline earth metal hydride, and a base-type ion exchange resin.

50. The process of claim 49, wherein the basic substance is a member selected from the group consisting of an alkali metal hydroxide and an alkaline earth metal hydroxide.

51. The process of claim 31, wherein the solvent is a mixed solvent of a lower alcohol selected from the group consisting of methanol and ethanol with an aliphatic hydrocarbon or an alicyclic hydrocarbon and/or an aromatic hydrocarbon.

52. The process of claim 51, wherein the lower alcohol is methanol.

53. The process of claim 51, wherein the aliphatic hydrocarbon is a member selected from the group consisting of pentane, hexane and heptane, the alicyclic hydrocarbon is a member selected from the group consisting cyclohexane and methylcyclohexane; and the aromatic hydrocarbon is a member selected from the group of benzene, toluene and xylene.

54. The process of claim 51, wherein the solvent is a mixed solvent of methanol, heptane and toluene.

55. The process of claim 51, 52, 53 or 54, wherein the basic substance used as a catalyst is a nitrogen-containing base or a phosphorus-containing base.

56. The process of claim 51, 52, 53, or 54, wherein the basic substance used as a catalyst is ammonia or an organic amine.

57. The process of claim 51, 52, 53 or 54, wherein the basic substance used as a catalyst is selected from the group consisting of an alkali metal hydroxide, an alkaline earth metal hydroxide, an alkali metal alcoholate, an alkaline earth metal alcoholate, an alkali metal amide, an alkaline earth metal amide, an alkali metal hydride, an alkaline earth metal hydride and a base-type ion exchange resin.

58. The process of claim 57, wherein the basic substance is selected from the group consisting of an alkali metal hydroxide and an alkaline earth metal hydroxide.

59. The process of claim 51, 52, 53 or 54, wherein the process includes removing the basic substance after the crystallization.

60. The process of claim 51, 52, 53 or 54, wherein the process includes neutralizing the basic substance with an acidic substance after the crystallization.

* * * * *